United States Patent [19]

Murakami et al.

[11] Patent Number: 4,882,326

[45] Date of Patent: Nov. 21, 1989

[54] PIPERIDINE COMPOUNDS AND PHARMACEUTICAL USES THEREOF

[75] Inventors: Shu Murakami, Fukuoka; Tsuguo Ikebe, Oita; Ichiro Hakamada, Oita; Osamu Yaoka, Oita, all of Japan

[73] Assignee: Yoshitomi Pharmaceutical Industries, Ltd., Osaka, Japan

[21] Appl. No.: 197,877

[22] Filed: May 24, 1988

[30] Foreign Application Priority Data

May 25, 1987 [JP] Japan .................. 62-129414
Oct. 14, 1987 [JP] Japan .................. 62-259379

[51] Int. Cl.$^4$ .................. A61K 31/55; C07D 281/02
[52] U.S. Cl. .................. 514/211; 514/213; 540/491; 540/523; 546/248; 546/246; 546/241; 546/233; 546/229
[58] Field of Search .................. 540/491, 523; 514/211, 514/213

[56] References Cited

U.S. PATENT DOCUMENTS

| | | | |
|---|---|---|---|
| 4,046,889 | 9/1977 | Ondetti et al. | 424/244 |
| 4,477,464 | 10/1984 | Slade et al. | 540/491 |
| 4,548,932 | 10/1985 | Sugihara et al. | 540/491 |
| 4,564,612 | 1/1986 | Sugihara et al. | 540/491 |
| 4,638,000 | 1/1987 | Sugihara et al. | 540/491 |

FOREIGN PATENT DOCUMENTS

| | | | |
|---|---|---|---|
| 0012401 | 6/1980 | European Pat. Off. | 548/532 |
| 0156455 | 10/1985 | European Pat. Off. | 540/491 |

OTHER PUBLICATIONS

Derwent Publications Ltd., J61148-171-A & EP 72-352, Drugs of the Future, vol. 8, No. 12, 1983, p. 1051.

*Primary Examiner*—Robert T. Bond
*Attorney, Agent, or Firm*—Sughrue, Mion, Zinn, Macpeak & Seas

[57] ABSTRACT

Piperidine compounds of the formula:

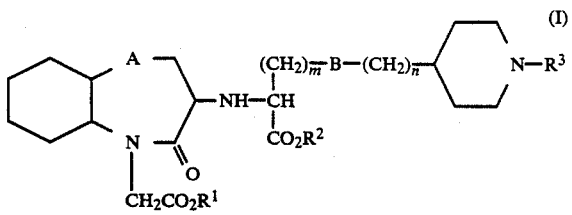

or isomers thereof as well as pharmaceutically acceptable salts and/or hydrate forms thereof, and piperidine compounds of the formula:

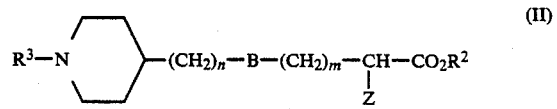

or isomers thereof as well as salt and/or hydrate forms thereof.

In the above formulae, A represents a methylene group, an oxygen atom or a sulfur atom; B represents an oxygen atom or a sulfur atom; $R^1$ and $R^2$ independently represent a hydrogen atom, a lower alkyl group or an aralkyl group; $R^3$ represents a hydrogen atom or an amino protecting group; Z represents an amino group or a protected amino group, a hydroxy group, or a reactive atom or group; m represents 1 or 2; and n represents the integer of 0 to 3.

Piperidine compounds (I) possess an inhibitory activity against angiotensin-converting enzyme, and exhibit a long lasting hypotensive activity and are useful as antihypertensive agents. Piperidine compounds (II) are useful as intermediates for said piperidine compounds (I).

3 Claims, No Drawings

PIPERIDINE COMPOUNDS AND PHARMACEUTICAL USES THEREOF

BACKGROUND OF THE INVENTION

The present invention relates to new piperidine compounds which are useful as therapeutic drugs for circulatory diseases such as hypertension and congestive heart failure, or isomers thereof as well as pharmaceutically acceptable salts thereof and the intermediates for their synthesis.

There have been reported a wide variety of hypotensive drugs whose mode of action is based on the inhibition of angiotensin-converting enzyme [Drugs of the Future, vol. 8, p. 1051 (1983)]. The representative examples thereof include oligopeptide compounds such as captopril (U.S. Pat. No. 4,046,889) and enalapril (European Patent Application No. 12401A). In addition, it has recently been found that nonpeptide compounds such as benzazepine derivatives or benzothiazepine compounds have a similar hypotensive effect (European Patent Application Nos. 72,352A and 156,455A, and Japanese Patent Application Publication (Unexamined) No. 148171/1986).

These hypotensive drugs are not always satisfactory in respect of effect certainty, action prolongation or adverse reaction, despite the fact that their dosing usually continues for a long period.

The present inventors made investigations to solve these problems; as a result, the inventors found that piperidine compounds or isomers thereof as well as salt and/or hydrate forms thereof inhibit an angiotensin-converting enzyme, and exhibit long lasting and excellent hypotensive activity, and completed this invention.

SUMMARY OF THE INVENTION

Accordingly, it is the object of the present invention to provide a novel piperidine compound possessing inhibitory activity on an angiotensin-converting enzyme and exhibiting long lasting and excellent hypotensive activity.

Another object of the present invention is to provide a pharmaceutical use of said piperidine compound.

Further object of the invention is to provide novel piperidine compounds which are useful as an intermediate for manufacturing the piperidine compound of the present invention.

DETAILED DESCRIPTION

The present invention relates to piperidine compounds of the formula:

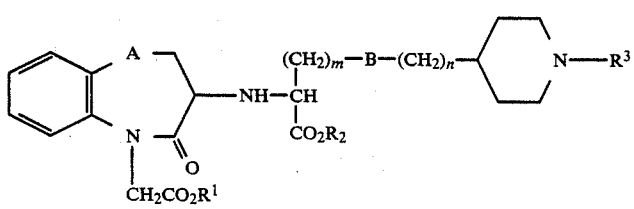

wherein A represents a methylene group, an oxygen atom or a sulfur atom; B represents an oxygen atom or a sulfur atom; $R^1$ and $R^2$ independently represent a hydrogen atom, a lower alkyl group or an aralkyl group; $R^3$ represents a hydrogen atom or an amino protecting group; m represents 1 or 2; and n represents and integer of 0 to 3, or an isomer thereof as well as pharmaceutically acceptable acid addition salts thereof.

The present invention also relates to a pharmaceutical composition which comprises the compound of formula (I) and a pharmaceutically acceptable additive.

Further, the present inventors have found that piperidine compounds of the formula:

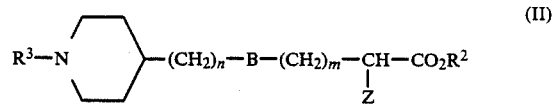

wherein Z represents an amino group, a protected amino group, a hydroxy group, or a reactive atom or group, and B, $R^2$, $R^3$, m and n are as defined above, or an isomers thereof as well as salts thereof are useful as important intermediates for manufacturing the compounds of formula (I).

The definitions of the symbols in the formulae (I) and (II) of the compounds of this invention are hereinafter described in more detail. A, B, m and n have the same definitions as above; and lower alkyl groups for $R^1$ and $R^2$ mean alkyl groups having 1 to 6 carbon atoms such as methyl, ethyl, propyl, isopropyl, butyl, tertiary butyl, pentyl, isopentyl, neopentyl and hexyl; aralkyl groups for $R^1$ and $R^2$ include benzyl, 1-phenylethyl, 2-phenylethyl, 3-phenylpropyl, diphenylmethyl and others. The amino protective group for $R^3$ is a protective group which is generally well-known in the organosynthetic chemistry field (e.g. ethoxycarbonyl, benzyloxycarbonyl, tertiary butoxycarbonyl, trifluoroacetyl, triphenylmethyl, diphenylmethyl or benzyl). The protected amino group for Z is an amino group protected by a protective group which is commonly used in the organosynthetic chemistry field such as ethoxycarbonyl, benzyloxycarbonyl or tertiary butoxycarbonyl, and it is preferable to choose a protective group which is more deprotectable than the other amino protective group for $R^3$. The reactive atom or group for Z includes a halogen atom (e.g. chlorine, bromine or iodine) and a sulfonyloxy group (e.g. methanesulfonyloxy, ethanesulfonyloxy, trifluoromethanesulfonyloxy, benzenesulfonyloxy, p-toluenesulfonyloxy, p-nitrobenzenesulfonyloxy or p-bromobenzenesulfonyloxy).

Having two asymmetric carbon atoms in their molecule, the compounds of formulae (I) and (II) can exist as an optically pure diastereoisomer, a racemate thereof or a mixture of diastereoisomers. The present invention embraces all these forms of stereoisomers.

The compounds of formulae (I) and (II) have an acidic group (in cases where $R^1$ or $R^2$ is a hydrogen atom) and a basic group in their molecules, being capable of forming salts with conventional organic acids, organic bases and also inorganic acids and inorganic bases; therefore, the pharmaceutically acceptable salts include all salts formed with these acids and bases. That is, said salts include salts with organic acids such as acetic acid, propionic acid, succinic acid, glycolic acid, lactic acid, malic acid, tartaric acid, citric acid, ascorbic acid, maleic acid, fumaric acid, methanesulfonic acid and p-toluenesulfonic acid; organic bases such as methylamine, diethylamine, triethylamine, dicyclohexylamine, triethanolamine, ethylenediamine, trishydroxymethylaminomethane, lysine, ornithine, arginine, guanidine, quinine and cinchonine; inorganic acids such as hydrochloric acid, hydrobromic acid, sulfuric acid, phosphoric acid and nitric acid; and inorganic bases such as ammonia, sodium, potassium, calcium, magnesium and zinc. The hydrate form includes, for example, hemihydrate, monohydrate, sesquihydrate, dihydrate or trihydrate.

Preferable compounds of the formula (I) are selected from the group consisting of 3-[1(R)-carboxy-2-{2-(4-piperidyl)ethylthio}ethyl]amino-2-oxo-2,3,4,5-tetrahydro-1H-1-benzazepine-1-acetic acid, 3-[1(R)-ethoxycarbonyl-2-{2-(4-piperidyl)ethylthio}ethyl]amino-2-oxo-2,3,4,5-tetrahydro-1H-1-benzazepine-1-acetic acid, 3(S)-[1(S)-ethoxycarbonyl-2-{2-(4-piperidyl)ethoxy}ethyl]amino-2-oxo-2,3,4,5-tetrahydro-1H-1-benzazepine-1-acetic acid, 3(R)-[1(S)-ethoxycarbonyl-2-{2-(4-piperidyl)ethoxy}ethyl]amino-4-oxo-2,3,4,5-tetrahydro-1,5-benzothiazepine-5-acetic acid, 3(S)-[1(S)-carboxy-2-{2-(4-piperidyl)ethoxy}ethyl]amino-2-oxo-2,3,4,5-tetrahydro-1H-1-benzazepine-1-acetic acid, 3(R)-[1(S)-carboxy-2-{2-(4-piperidyl)ethoxy}ethyl]amino-4-oxo-2,3,4,5-tetrahydro-1,5-benzothiazepine-5-acetic acid, 3-[1(R)-carboxy-2-(4-piperidyl)methylthioethyl]amino-2-oxo-2,3,4,5-tetrahydro-1H-1-benzazepine-1-acetic acid, 3(S)-[1(S)-carboxy-2-{3-(4-piperidyl)propoxy}ethyl]amino-2-oxo-2,3,4,5-tetrahydro-1H-1-benzazepine-1-acetic acid, 3(R)-[1(S)-carboxy-2-{3-(4-piperidyl)propoxy}ethyl]amino-4-oxo-2,3,4,5-tetrahydro-1,5-benzothiazepine-5-acetic acid, and isomers thereof as well as a pharmaceutically acceptable salt and/or hydrate form thereof.

The compounds of formula (I) of the present invention can be produced as follows:

The compounds (I) of the present invention wherein $R^3$ is not a hydrogen atom can be produced by subjecting to reductive condensation of a compound of the formula:

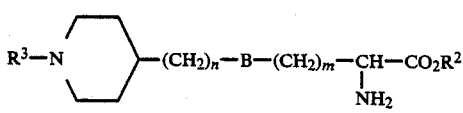
(III)

wherein B, $R^2$, m and n are as defined above and $R^3$ is as defined above (other than a hydrogen atom), and a compound of the formula:

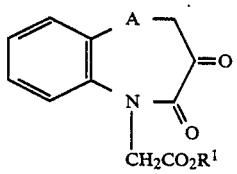
(IV)

wherein A and $R^1$ are as defined above, or by subjecting to condensation a compound of the formula:

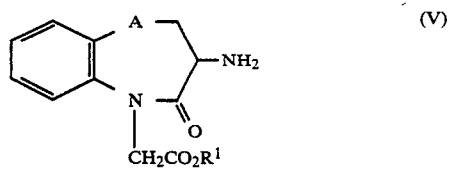
(V)

wherein A and $R^1$ are as defined above, and a compound of the formula:

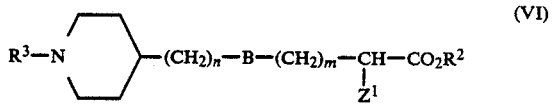
(VI)

wherein B, $R^2$, $R^3$, m and n are as defined for the formula (III); $Z^1$ represents the reactive atom or group for Z.

The compounds (I) of the present invention wherein $R^3$ is a hydrogen atom can be produced by subjecting to a deprotection reaction the compounds having an amino protective group on the piperidine ring which can be synthesized by either of the above-mentioned methods.

The reductive condensation reaction of the compounds (III) and (IV) is carried out in the presence of a reducing agent in an inert solvent, or, in advance, by deriving the corresponding imine (Schiff base) in the presence of a catalytic amount of a dehydrating condensation agent, and then adding the reducing agent. Solvents which can be used include water and organic solvents such as methanol, ethanol, tetrahydrofuran, diethyl ether, dioxane, dichloromethane, chloroform, ethyl acetate, benzene, toluene, dimethylformamide, dimethylacetamide and acetic acid.

As reductive conditions for the reaction, there may be included catalytic hydrogen reduction using a metal such as platinum, palladium, Raney nickel or rhodium, or a mixture of any of them and a carrier as the catalyst; reduction with a metal hydride such as lithium aluminum hydride, sodium cyanoborohydride, sodium borohydride or potassium borohydride; reduction with metallic sodium, metallic magnesium or the like and an alcohol such as methanol or ethanol; and reduction with a metal such as iron or zinc and an acid such as hydrochloric acid or acetic acid. In particular in the case of reduction with a metal hydride such as sodium cyanoborohydride, it is desirable to carry out the reaction in the presence of an acid such as hydrochloric acid or acetic acid. There is no particular limitation on the dehydrating condensation agents used as required; as dehydrating condensation agents, there may include inorganic acids (hydrochloric acid, sulfuric acid, nitric acid, etc.) organic acids (methanesulfonic acid, p-toluenesulfonic acid, etc.), Lewis acids (aluminum chloride, tin tetrachloride, iron chloride, zinc chloride, trifluoroborane etherate, dibutyltin dichloride, etc.), and molecular sieves.

Reaction temperature for the reductive condensation varies according to the reagents and solvents used, and a temperature of −20° to 100° C. is generally preferred. The purpose of this reaction can be satisfactorily accomplished under normal pressure, and also the reaction can be carried out under increased or reduced pressure as well.

On the other hand, condensation of the compounds (V) and (VI) carried out in the presence or absence of a base in an inert solvent (e.g. hydrocarbons such as hexane, benzene and toluene; hydrocarbon halides such as chloroform and dichloromethane; ethers such as tetrahydrofuran and dioxane; esters such as ethyl acetate; ketones such as acetone; amides such as dimethylformamide and dimethylacetamide; acetonitrile; dimethylsulfoxide) or without a solvent.

There is no particular limitation on the bases used as required; as examples of preferable bases, example may be made of alkali metal carbonates such as sodium carbonate and potassium carbonate; alkali metal hydrogen carbonates such as sodium hydrogen carbonate and potassium hydrogen carbonate; alkali metal hydrides such as sodium hydride; and organic bases such as triethylamine, pyridine, picoline and N-methylmorpholine. Alkali metal hydroxides such as sodium hydroxide and potassium hydroxide may also be used in a two-phase system of water and any one of the above-mentioned organic solvents in the presence of a phase-transfer catalyst such as tetrabutylammonium bromide or benzyltriethylammonium iodide. The reaction is usually carried out at 0° to 150° C.

The deaminoprotection reaction for the compound (I) wherein $R^3$ is not a hydrogen atom is carried out by the addition of a widely used deprotecting agent (e.g. acids such as hydrobromic acid, hydrochloric acid, hydrofluoric acid, trifluoroacetic acid and trifluoromethanesulfonic acid or bases such as ammonia, sodium hydroxide and potassium hydroxide) as appropriate for the type of the protective group $R^3$, or by a reductive elimination method (e.g. hydrogenation using palladium-black catalyst and the metallic sodium-liquid ammonia method).

Of the compounds of the general formula (I), carboxylic acid compounds in which $R^1$ and/or $R^2$ is a hydrogen atom or a salt can be produced by hydrolyzing the corresponding ester compounds produced by any one of the above-mentioned methods with an acid or a base, or by reductively eliminating the ester groups.

The reaction product thus obtained can be purified by a conventional separation and purification method such as recrystallization, column chromatography, etc. In particular the compounds of formula (I) which comprise diasteromeric isomers can easily be separated. That is, two forms of isomers can be obtained by deriving the compounds of formula (I) without racemization using either of the optical isomers of the compounds of formula (III), (V) or (VI) in a reaction, their separation being conducted by the fractional crystallization method or various chromatographies or by the fractional crystallization method of salts formed with the suitable acid or base as mentioned above. In condensation of the compounds of formulae (V) and (VI), the compounds of formula (I) can of course be obtained as a single form of isomer by the use of either optical isomer alone for each compound.

In addition, salts of the compounds (I) can be obtained in the course of the reaction itself for producing the compounds (I), and it is also possible to form salts of the compounds (I) by adding an acid, alkali or base as required.

The starting material compounds of formulae (IV) and (V) can be prepared by a known production method [J. Med. Chem., vol. 28, pp. 1511, 1517 and 1603 (1985)] or by a similar method.

The new starting material compounds of formula (III) can be produced, for example, by the reaction scheme shown below.

Reaction scheme I

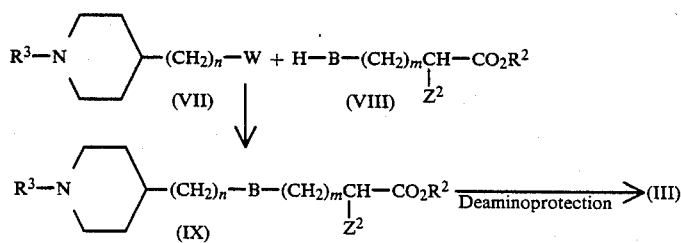

wherein B, $R^2$, $R^3$, $R^4$, m and n are as defined for the formula (III); $Z^2$ represents an amino group or a protected amino group; W represents a halogen atom or a sulfonyloxy group (such examples are the same as defined for Z).

According to the method shown in the reaction scheme [I], the compound (III) can be obtained directly by condensation of the piperidine derivative (VII) and the amino acid derivative (VIII) when $Z^2$ is an amino group. When $Z^2$ is not an amino group, the compound (III) can be obtained by deriving the compound (IX) in the same condensation of the compounds (VII) and (VIII), and then selectively eliminating the protected amino group from the derivative (IX). The condensation is carried out in an appropriate solvent (e.g. water; alcohols such as methanol, ethanol, isopropyl alcohol and tertiary butanol; ethers such as diethyl ether, tetrahydrofuran and dioxane; hydrocarbon halides such as chloroform and dichloromethane; aprotic polar solvents such as acetonitrile, dimethylformamide, dimethylacetamide, dimethylsulfoxide and hexamethylphosphorotriamide) in the presence of a deacidifying agent (e.g., alkali metal hydroxides such as sodium hydroxide and potassium hydroxide; alkali metal carbonates or alkali metal hydrogen carbonates such as sodium carbonate, potassium carbonate, sodium hydrogen carbonate and potassium hydrogen carbonate; alkali metal alkoxides such as sodium methoxide, sodium ethoxide and potassium tert-butoxide; alkali metal hydrides such as sodium hydride; and organic tertiary amines such as triethylamine, pyridine, N-methylmorpholine and 1,8-diazabicyclo[5.4.0]undecan-7-ene) at a reaction temperature of about 0° to 100° C. Although the reaction conditions may vary according to the type of the other amino protective group $R^3$, the selective elimination reaction for the amino protective group $Z^2$ can be carried out by the addition of a widely used deaminoprotecting agent (e.g. acids such as hydrobromic acid, hydrochloric acid, hydrofluoric acid, trifluoroacetic acid and trifluoromethanesulfonic acid; and bases such as ammonia, sodium hydroxide and potassium hydroxide) or by a reductive method (e.g. hydrogenation using palladium-black catalyst and the metallic sodium-liquid ammonia method). The piperidine derivative (VI) used as a starting material in the reaction scheme [I] can be synthesized by a known method.

On the other hand, the new starting material compound of formula (VI) can be, for example, prepared according to the reaction scheme shown below from the compound (III) obtained by the reaction scheme [I].

Reaction scheme II

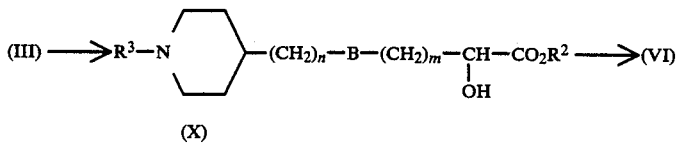

wherein B, $R^2$, $R^3$, m and n ae as defined for the formula (VI).

According to the method shown in the reaction scheme [II], the compound (X) can be obtained by treating the compound (III) with sodium nitrite in an aqueous acidic solution (aqueous acetic acid, aqueous hydrochloric acid, aqueous sulfuric acid, etc.). The compound (X) can be converted to the reactive derivative (VI) by further subjecting the compound (X) to the known halogenation reaction or sulfonylation reaction.

In preparing the compounds of formulae (III), (IX) or (X), mutual conversion between the compounds having a hydrogen atom for $R^2$ (carboxylic acid derivatives) and the compounds in which $R^2$ is not a hydrogen atom (ester derivatives) is of course possible by a well-known hydrolysis or hydrogenolysis process from the ester derivatives to the carboxylic derivatives and by a conventional esterification reaction from the carboxylic acid derivatives to the ester derivatives.

The following experiments will illustrate the pharmacological actions of the compounds (I) of the present invention.

Experiment 1: Inhibitory effect on angiotensin I-induced constriction in isolated guinea pig ileum According to the method of Goldberg et al (J. Pharmacol. Exp. Ther., vol. 204, No. 2, p. 271, 1977), the inhibitory effect on angiotensin I converting enzyme was indirectly examined as an antagonistic activity on angiotensin I-induced constriction in isolated guinea pig ileum preparation. Guinea pig ileum preparations, in the presence of 1 g load, were suspended in Magnus bath filled with Kreb's solution containing atropine and maintained at 37° C. by warming, and then bubbled with a mixed gas (95%$O_2$+5%$CO_2$). Angiotensin I ($10^{-8}$M)-induced constrictions were measured with a recorder through a force displacement transducer (Nippon Denki San-ei, 45169A). Inhibitory rates of the test compounds were indicated on a graph and the rate of 50% inhibition ($IC_{50}$) was calculated. From these results, the $IC_{50}$ value was $1.6 \times 10^{-9}$M for the compound of Example 7. On the other hand, the $IC_{50}$ value was $3.5 \times 10^{-9}$M for 3(R)-[1(S)-carboxy-5-(4-piperidyl)pentyl]amino-4-oxo-2,3,4,5-tetrahydro-1,5-benzothiazepine-5-acetic acid (hereinafter referred to as CV-5975) as the compound for comparison.

Experiment 2: Effect on angiotensin I-induced pressor response in rats

Groups of 10 Wistar male rats weighing about 200 g were implanted with a catheter into the left carotid artery and femoral vein under ether anesthesia. More than 24 hours after operation, mean blood pressure was measured from the carotid artery with a pressure transducer (Nippon Denki San-ei, 142 type). Angiotensin I (300 ng/kg) was injected to the left femoral vein through catheter to induce pressor response. Then 10 mg/kg of the test compounds, suspended in 0.5% methylcellulose solution, were given orally. At every hour between 1 to 10 hours, and 24 hours after the administration, the pressor response was examined by the injection of angiotensin I. The inhibitory rate (%) against the pressor responses was determined and the results were summarized in Table 1. The values in the Table represent "mean value±standard error".

The results shown in Table 1 suggest that the compound of Example 7 of the present invention exhibits stronger inhibitory action against the angiotensin I-induced pressor response and more long-lasting effect than C-5975.

TABLE 1

| | Inhibitory rate (%) of pressor response to angiotensin I at each hour | |
|---|---|---|
| | Test Compound | |
| | The compound of example 7 | CV-5975 |
| Time (hour) | Dose (mg/kg, p.o.) | |
| | 10 | 10 |
| 1 | −96 ± 2 | −95 ± 3 |
| 2 | −100 ± 0 | −95 ± 3 |
| 3 | −94 ± 5 | −89 ± 7 |
| 4 | −97 ± 3 | −85 ± 7 |
| 5 | −100 ± 0 | −82 ± 8 |
| 6 | −100 ± 0 | −89 ± 6 |
| 7 | −100 ± 0 | −86 ± 6 |
| 8 | −98 ± 2 | −80 ± 7 |
| 9 | −100 ± 0 | −84 ± 7 |
| 10 | −90 ± 6 | −75 ± 9 |
| 24 | −77 ± 10 | −45 ± 10 |

Toxicity Experiment

All animals survived even at the dose of 100 mg/kg (i.p., mice) and (p.o., rats) of the compound of Example 7.

Inhibiting activities of angiotensin-converting enzyme and kininase II and exhibiting a long lasting hypotensive action with low toxicity, the piperidine compounds of formula (I) of the present invention, isomers thereof and pharmaceutically acceptable salts thereof are useful as diagnostic, preventive or therapeutic drugs for hypertension and hypertension-related circulartory diseases such as congestive heart failure and cerebral apoplexy. Further, the compounds of formula (II) are useful as an intermediate for manufacturing the compounds of formula (I).

When used as the above-mentioned drugs, the compounds of the present invention can be orally or parenterally administered as a therapeutically effective amount in the form of powder, granules, tablets, capsules, injections, etc., singly or in combination with pharmaceutically acceptable additives such as carriers, excipients, diluents, etc., which are chosen as appropriate. Such drugs comprise a therapeutically effective amount of the compound of the present invention. Although varying according to the type of the target diseases, symptoms and the compounds used, dose is usually about 1 to 100 mg a day for an adult in the case of oral administration.

Formulation Example

The compounds of the present invention when used as therapeutic drugs for hypertension, can be formulated to the following compositions:

| (a) Tablets | |
|---|---|
| Compound of the invention | 10 mg |
| Lactose | 150 mg |
| Crystalline cellulose | 50 mg |
| Calcium carboxymethylcellulose | 7 mg |
| Magnesium stearate | 3 mg |
| Total | 220 mg |

The tablets may be coated with a film as is usually used and may also be coated with sugar.

| (b) Granules | |
|---|---|
| Compound of the invention | 10 mg |
| Polyvinylpyrrolidone | 25 mg |
| Lactose | 405 mg |
| Hydroxypropylcellulose | 50 mg |
| Talc | 10 mg |
| Total | 500 mg |
| (c) Powder | |
| Compound of the invention | 10 mg |
| Lactose | 600 mg |
| Starch | 360 mg |
| Colloidal silica | 30 mg |
| Total | 1000 mg |
| (d) Capsules | |
| Compound of the invention | 10 mg |
| Lactose | 122 mg |
| Crystalline cellulose | 56 mg |
| Colloidal silica | 2 mg |
| Total | 190 mg |

(e) Injection

The injection contains the compound of the invention in an amount of 1 to 30 mg in 1 ml of aqueous solution (pH 6.5 to 7) and is prepared under aseptic conditions.

The present invention will now be described in more detail by means of the following reference examples and working examples, but the invention is not limited thereto.

Reference Example 1

In a nitrogen gas flow, 562 mg of L-cysteine hydrochloride monohydrate is dissolved in an aqueous solution of 2N sodium hydroxide. To the resulting solution, 5 ml of a tetrohydrofuran solution containing 1.2 g of 2-(1-benzyloxycarbonyl-4-piperidyl)ethyl iodide is added, and stirred for 1.5 hours at room temperature. Then, 3 ml of ethanol is further added, and stirred for 2 hours. The reaction solvent is distilled off under reduced pressure. To the residue, water and ether are added, and the mixture is shaken. The water layer is separated and adjusted to pH 5 with 2N aqueous hydrochloric acid to precipitate crystals. The crystals are recrystallized from methanol to give 0.8 g of S-[2-(1-benzyloxycarbonyl-4-piperidyl)ethyl]-L-cysteine having a melting point of 185° to 188° C.

Reference Example 2

In a nitrogen gas flow, 8.3 g of L-cysteine ethyl ester hydrochloride is added to a sodium ethoxide solution prepared by adding 2 g of metallic sodium to 80 ml of absolute ethanol. After stirring for 1 hours at room temperature, 80 ml of an ethanol solution containing 18.4 g of 2-(1-benzyloxycarbonyl-4-piperidyl)ethyl iodide is added dropwise to this reaction mixture. After stirring for 1 hour at room temperature, the reaction liquid is concentrated under reduced pressure. To the resulting residue, ice-cold water is added. After extracting with ether, the organic layer is washed with water, and dried over magnesium sulfate. Thereafter, the solvent is distilled off under reduced pressure to give 16.3 g of oily S-[2-(1-benzyloxycarbonyl-4-piperidyl)ethyl]-L-cysteine ethyl ester.

NMR spectrum [CDCl$_3$, tetramethylsilane internal standard (ppm)]: $\delta$=0.8–1.9(m, 7H), 1.3(t, 3H), 2.4–3.0(m, 6H), 3.69(dd, 1H), 3.9–4.4(m, 4H), 5.12(s, 2H), 7.33(s, 5H)

Reference Example 3

To 1.2 l of a dimethylformamide solution containing 48 g of N-(tert-butoxycarbonyl)-L-serine, 20.7 g of 60% oily sodium hydride is added under cooling with ice, and stirred. Reaction temperature is gradually raised to room temperature, and after the cease of hydrogen gas generation, 87.7 g of 2-(1-benzyloxycarbonyl-4-piperidyl)ethyl iodide is added.

After stirring for 5 hours at room temperature, the reaction solvent is distilled off under reduced pressure. To the resulting residue, ice-cold water is added, and the aqueous layer is washed with ether. This aqueous layer is adjusted to pH 3 with 1.2N aqueous hydrochloric acid, and extracted with ethyl acetate. The organic layer is washed with water, and dried over magnesium sulfate, and then concentrated under reduced pressure. The resulting oily residue is purified by silica gel column chromatography (chloroform:methanol=20:1) to give 17 g of oily O-[2-(1-benzyloxycarbonyl-4-piperidyl)ethyl]-N-(tert-butoxycarbonyl)-L-serine.

NMR spectrum (CDCl$_3$; ppm): $\delta$=0.8–1.8(br m, 7H), 1.43(s, 9H), 2.72(br t, 2H), 3.3–4.0(br m, 4H), 3.95–4.56(br m, 3H), 5.12(s, 5H), 7.33(s, 5H)

$[\alpha]_D$= +11.7° (c=3.0%, methanol)

Reference Example 4

9.6 g of N-(tert-butoxycarbonyl)-D-serine, in place of N-(tert-butoxycarbonyl)-L-serine, is subjected to the same reaction procedure as in Reference Example 3 to give 4.4 g of oily O-[2-(1-benzyloxycarbonyl-4-piperidyl)ethyl]-N-(tert-butoxycarbonyl)-D-serine.

NMR spectrum (CDCl$_3$; ppm): $\delta$=0.8–1.8(br m, 7H), 1.43(s, 9H), 2.72(br t, 2H), 3.3–4.0(br m, 4H), 3.95–4.56(br m, 3H), 5.12(s, 2H), 7.33(s, 5H)

Reference Example 5

17 g of O-[2-(1-benzyloxycarbonyl-4-piperidyl)ethyl]-N-(tert-butoxycarbonyl)-L-serine obtained in Reference Example 3 is dissolved in 350 ml of dimethylformamide. To the resulting solution, 8.5 ml of ethyl bromide and 2.6 g of potassium carbonate are added, and stirred overnight at room temperature. After filtering the reaction liquid, the solvent is distilled off under reduced pressure. To the residue, ice-cold water and ethyl acetate are added, and this mixture is shaken well. The ethyl acetate layer is washed with saturated saline, and dried over magnesium sulfate; thereafter, the solvent is distilled off under reduced pressure to give 16 g of O-[2-(1-benzyloxy-carbonyl-4-piperidyl)ethyl]-N-(tert-butoxycarbonyl)-L-serine ethyl ester as an oily substance.

NMR spectrum (CDCl$_3$; ppm): $\delta$=1.27(t, 3H), 1.46(s, 9H), 2.72(br t, 2H), 3.45(t, 2H), 3.4–3.9(m, 2H), 5.11(s, 2H), 7.36(s, 5H)

Reference Example 6

To 16 g of O-[2-(1-benzyloxycarbonyl-4-piperidyl)ethyl]-N-(tert-butoxycarbonyl)-L-serine ethyl ester obtained in Reference Example 5, 50 ml of trifluoroacetic acid is added at room temperature, and stirred for 2 hours. After distilling off the solvent under reduced pressure, ice-cold water is added to the residue. The mixture is then rendered alkaline with sodium hydrogen carbonate, followed by extracting with ethyl acetate. The organic layer is washed with saturated saline, and dried over magnesium sulfate; thereafter, the solvent is distilled off under reduced pressure to give 13 g of O-[2-(1-benzyloxycarbonyl-4-piperidyl)ethyl]-L-serine ethyl ester as an oily substance.

NMR spectrum (CDCl$_3$; ppm): $\delta$=1.28(t, 3H), 2.72(br t, 2H), 3.48(t, 2H), 5.1(s, 2H), 7.33(s, 5H)

$[\alpha]_D$= +1.6° (c=1.0%, methanol)

Reference Example 7

To 4.4 g of O-[2-(1-benzyloxycarbonyl-4-piperidyl)ethyl]-N-(tert-butoxycarbonyl)-D-serine obtained in Reference Example 4, 40 ml of trifluoroacetic acid is added, and stirred for 1 hour at room temperature. The reaction solvent is distilled off under reduced pressure, and the resulting residue is dissolved in 40 ml of 50% aqueous acetic acid. To the resulting solution, 40 ml of an aqueous solution of 50% acetic acid containing 5 g of sodium nitrite is added at room temperature, and stirred for 1 hour. The reaction liquid is concenrated under reduced pressure. To the resulting residue, ice-cold water is added, and the mixture is adjusted to pH 2 with aqueous dilute hydrochloric acid. After extracting with ethyl acetate, the organic layer is washed with aqueous dilute hydrochloric acid and then with water. After drying the organic layer, the solvent is distilled off under reduced pressure. The resulting residue is purified by silica gel column chromatography (ethyl acetate:ethanol:water=20:1:0.5) to give 2.7 g of 3-[2-(1-benzyloxycarbonyl-4-piperidyl)-ethoxy]-2(R)-hydroxypropionic acid as an oily substance.

NMR spectrum (CDCl$_3$; ppm): $\delta$=0.8–1.85(br, 7H), 2.78(br t, 2H), 3.4–4.0(m, 4H), 4.0–4.5(br m, 3H), 5.12(s, 2H), 7.36(s, 5H)

Reference Example 8

0.5 g of O-[2-(1-benzyloxycarbonyl-4-piperidyl)ethyl]-N-(tert-butoxycarbonyl)-L-serine, in place of O-[2-(1-benzyloxycarbonyl-4-piperidyl)ethyl]-N-(tert-butoxycarbonyl)-D-serine, is subjected to the same reaction procedure and purification treatment as in Reference Example 7 to give 380 mg of 3-[2-(1-benzyloxycarbonyl-4-piperidyl)ethoxy]-2(S)-hydroxypropionic acid as an oily substance.

NMR spectrum (CDCl$_3$; ppm): $\delta$=0.8–1.85(br, 7H), 2.78(br t, 2H), 3.4–4.0(m, 4H), 4.0–4.5(br m, 3H), 5.12(s, 2H), 7.36(s, 5H)

Reference Example 9

500 mg of 3-[2-(1-benzyloxycarbonyl-4-piperidyl)ethoxy]-2(R)-hydroxypropionic acid obtained in Reference Example 7, 500 mg of ethyl bromide and 200 mg of potassium carbonate are placed in 10 ml of dimethylformamide, and stirred for 14 hours at room temperature. The reaction mixture is concentrated under reduced pressure. To the resulting residue, ice-cold water and ethyl acetate are added, and this mixture is shaken. The ethyl acetate layer is washed with saturated saline, and dried over magnesium sulfate; thereafter, the solvent is distilled off under reduced pressure to give 360 mg of oily ethyl 3-[2-(1-benzyloxycarbonyl-4-piperidyl)ethoxy]-2(R)-hydroxypropionate.

NMR spectrum (CDCl$_3$; ppm): $\delta$=1.28(t, 3H), 2.76(br t, 2H), 3.52(t, 2H), 3.7(d, 2H), 5.12(s, 2H), 7.33(s, 5H)

$[\alpha]_D$= +3.0° (c=0.7%, chloroform)

Reference Example 10

350 mg of ethyl 3-[2-(1-benzyloxycarbonyl-4-piperidyl)ethoxy]-2(R)-hydroxypropionate obtained in Reference Example 9 is dissolved in 5 ml of pyridine. To the resulting solution, 320 mg of methanesulfonyl chloride is added dropwise under cooling with ice. After stirring for 1.5 hours at room temperature, 0.5 ml of water is added, and further stirring for 1 hour conducted. To the reaction liquid, a large amount of water and ethyl acetate are added, and the mixture is shaken well. The ethyl acetate layer is washed with dilute hydrochloric acid, saturated saline, saturated sodium hydrogencarbonate and then with water, and dried over magnesium sulfate; thereafter, the solvent is distilled off under reduced pressure to give 310 mg of oily ethyl 3-[2-(1-benzyloxycarbonyl-4-piperidyl)ethoxy]-2(R)-methanesulfonyloxypropionate.

NMR spectrum (CDCl$_3$; ppm): $\delta$=2.78(br t, 2H), 3.2(s, 3H), 3.3–3.8(m, 2H), 3.9(d, 2H), 5.12(s, 2H), 5.18(t, 1H), 7.34(s, 5H)

Reference Example 11

3.6 g of 1-benzyloxycarbonyl-4-piperidylmethyl iodide, in place of 2-(1-benzyloxycarbonyl-4-piperidyl)ethyl iodide, is subjected to the same reaction and treatment procedures as in Reference Example 1 to give 1.67 g of S-(1-benzyloxycarbonyl-4-piperidylmethyl)-L-cysteine having a melting point of 187° to 190° C.

Reference Example 12

25.1 g of 1-benzyloxycarbonyl-4-piperidylmethyl iodide, in place of 2-(1-benzyloxycarbonyl-4-piperidyl)ethyl iodide, is subjected to the same reaction and treatment procedures as in Reference Example 2 to give 24.8 g of oily S-(1-benzyloxycarbonyl-4-piperidylmethyl)-L-cysteine ethyl ester.

NMR spectrum (CDCl$_3$; ppm): $\delta$=1.3(t, 3H), 2.49(d, 2H), 3.68(dd, 1H), 4.0–4.4(m, 4H), 5.12(s, 2H), 7.35(s, 5H)

Reference Example 13

7.7 g of 3-(1-benzyloxycarbonyl-4-piperidyl)propyl iodide, in place of 2-(1-benzyloxycarbonyl-4-piperidyl)ethyl iodide, is subjected to the same reaction and treatment procedures as in Reference Example 4 to give 3.3 g of oily O-[3-(1-benzyloxycarbonyl-4-piperidyl)-propyl]-N-(tert-butoxycarbonyl)-D-serine.

NMR spectrum (CDCl$_3$; ppm): δ=0.8-1.9(br m, 9H), 1.43(s, 9H), 2.74(br t, 2H), 3.3-4.6(m, 7H), 5.12(s, 2H), 5.4(1H), 7.33(s, 5H), 8.62(br s, 1H)

[α]$_D$=−8.4° (c=0.5%, methanol)

Reference Example 14

37 g of O-[3-(1-benzyloxycarbonyl-4-piperidyl)-propyl]-N-(tert-butoxycarbonyl)-D-serine obtained in Reference Example 13 is added to 350 ml of trifluoroacetic acid, and stirred for 1 hour at room temperature. The reaction solvent is distilled off under reduced pressure, and the resulting residue is dissolved in 500 ml of 60% aqueous acetic acid. To the resulting solution, 150 ml of an aqueous solution containing 38 g of sodium nitrite is added at room temperature; after stirring for 1 hour, the mixture is kept standing overnight. The reaction liquid is concentrated under reduced pressure to about half volume. To the resulting residual liquid, 100 ml of cool 4N aqueous hydrochloric acid is added. After extracting with ethyl acetate, the organic layer is washed with water and dried. The solvent is distilled off under reduced pressure, and the resulting residue is dissolved in 50 ml of ethanol. To the resulting solution, 2N aqueous sodium hydroxide is added, and the system warmed for 0.5 hour; thereafter, the ethanol is distilled off under reduced pressure. The resulting residual liquid is adjusted to pH 1 with cool aqueous hydrochloric acid. After extracting with ethyl acetate, the organic layer is washed with water and dried, and then the solvent is distilled off to give 10 g of oily 3-[3-(1-benzyloxycarbonyl-4-piperidyl)propoxy]-2(R)-hydroxypropionic acid.

Reference Example 15

10 g of 3-[3-(1-benzyloxycarbonyl-4-piperidyl)-propoxy]-2(R)-hydroxypropionic acid obtained in Reference Example 14, in place of 3-[2-(1-benzyloxycarbonyl-4-piperidyl)ethoxy]-2(R)-hydroxypropionic acid, is subjected to the same reaction and treatment procedures as in Reference Example 9 to give 4.8 g of oily ethyl 3-[3-(1-benzyloxycarbonyl-4-piperidyl)propoxy]-2(R)-hydroxypropionate.

NMR spectrum (CDCl$_3$; ppm): δ=1.3(t, 3H), 2.76(br t, 2H), 3.48(t, 2H), 3.7(d, 2H), 5.12(s, 2H), 7.33(s, 5H)

[α]$_D$=+3.63° (c=0.5%, chloroform)

Reference Example 16

4.8 g of ethyl 3-[3-(1-benzyloxycarbonyl-4-piperidyl)-propoxy]-2(R)-hydroxypropionate obtained in Reference Example 15, in place of ethyl 3-[2-(1-benzyloxycarbonyl-4-piperidyl)ethoxy]-2(R)-hydroxypropionate, is subjected to the same reaction and treatment procedures as in Reference Example 10 to give 4.8 g of oily ethyl 3-[3-(1-benzyloxycarbonyl-4-piperidyl)-propoxy]-2(R)-methanesulfonyloxypropionate.

NMR spectrum (CDCl$_3$; ppm): δ=2.74(br t, 2H), 3.17(s, 3H), 3.3-3.7(m, 2H), 3.86(d, 2H), 5.12(s, 2H), 7.33(s, 5H)

Reference Example 17

3.7 g of 3-[2-(1-benzyloxycarbonyl-4-piperidyl)ethylthio]-2(S)-hydroxypropionic acid, in place of 3-[2-(1-benzyloxycarbonyl-4-piperidyl)ethoxy]-2(R)-hydroxypropionic acid, is subjected to the same reaction and treatment procedures as in Reference Example 9 to give 2.0 g of oily ethyl 3-[2-(1-benzyloxycarbonyl-4-piperidyl)ethylthio]-2(S)-hydroxypropionate.

NMR spectrum (CDCl$_3$; ppm): δ=1.3(t, 3H), 2.9(t, 2H), 5.1(s, 2H), 7.33(s, 5H)

[α]$_D$: +13.7° (c=1%, chloroform)

EXAMPLE 1

2.6 g of S-[2-(1-benzyloxycarbonyl-4-piperidyl)ethyl]-L-cysteine ethyl ester obtained in Reference Example 2, 1.7 g of ethyl 2,3-dioxo-2,3,4,5-tetrahydro-1H-1-benzazepine-1-acetate prepared by a known method and 100 mg of dibutyltin dichloride are dissolved in 130 ml of chloroform; the resulting solution is stirred and refluxed for 22 hours with removing water. After distilling off the reaction solvent under reduced pressure, the residue is dissolved in a mixed solvent of 50 ml of methanol and 10 ml of acetic acid. Under cooling with ice, 550 mg of sodium cyanoborohydride is added to this solution, and the system stirred. Reaction temperature is gradually raised to room temperature; 2 hours later, the reaction liquid is acidified with 1.7 ml of concentrated hydrochloric acid. To the residue obtained by concentration under reduced pressure, a saturated aqueous solution of sodium hydrogen carbonate and chloroform are added, and this mixture is shaken well. The chloroform layer is washed with water and dried over magnesium sulfate; thereafter, the solvent is distilled off under reduced pressure. The resulting residue is separated and purified by silica gel column chromatography (hexane:ethyl acetate=4:3) to give 1.5 g of the A-isomer (Rf=0.40; ethyl acetate:hexane=2:1) of ethyl 3-[2-{2-(1-benzyloxycarbonyl-4-piperidyl)ethylthio}-1(R)-ethoxycarbonylethyl]amino-2-oxo-2,3,4,5-tetrahydro-1H-1-benzazepine-1-acetate and 1.3 g of the B-isomer (Rf=0.35; the same developing solvent as above) each as an oily substance.

NMR spectrum (CDCl$_3$; ppm): A-Isomer, δ=1.24(t and t, 6H), 3.0-3.56(m, 3H), 4,4(d, 1H), 4.6(d, 1H), 5.12(s, 2H), 6.8-7.4(m, 4H), 7.33(s, 5H); B-Isomer, δ=1.1(t, 3H), 1.24(t, 3H), 3.0-3.5(m, 3H), 4.4(d, 1H), 4.6(d, 1H), 5.12(s, 2H), 6.9-7.4(m, 4H), 7.33(s, 5H)

[α]$_D$: A-Isomer, +93.7° (c=0.5%, methanol): B-isomer, −52.0° (c=1%, methanol)

EXAMPLE 2

12.9 g of S-[2-(1-benzyloxycarbonyl-4-piperidyl)ethyl]-L-cysteine ethyl ester, 9.0 g of tert-butyl 2,3-dioxo-2,3,4,5-tetrahydro-1H-1-benzazepine-1-acetate prepared by a known method and 500 mg of dibutyltin dichloride are dissolved in 600 ml of chloroform, and this solution is stirred and refluxed for 27 hours with removing water. After distilling off the reaction solvent under reduced pressure, the residue is dissolved in a mixed solvent of 250 ml of methanol and 46 ml of acetic acid. To the resulting solution, 1.9 g of sodium cyanoborohydride is added at room temperature, and the system stirred. Seventy hours later, ice-cooled aqueous dilute hydrochloric acid is added to the residue obtained by concentration under reduced pressure, and this mixture is kept standing. After neutralization with sodium hydrogen carbonate, ethyl acetate is added, and the mixture is shaken well. The organic layer is washed with water and dried; thereafter, the solvent is distilled off under reduced pressure. The resulting residue is separated and purified by silica gel column chromatography (hexane:ethyl acetate=4:3) to give 5.5 g of the A-isomer (Rf=0.47; ethyl acetate:n-hexane=2:1) of tert-butyl of 3-[2-{2-(1-benzyloxycarbonyl-4-piperidyl- )ethylthio}-1(R)-ethoxycarbonylethyl]amino-2-oxo-2,3,4,5-tetrahydro-1H-1-benzazepine-1-acetate and 4.1 g of the B-isomer (Rf=0.40; the same developing solvent as above) each as an oily substance.

NMR spectrum (CDCl$_3$; ppm): A-Isomer, δ=1.24(t, 3H), 1.42(s, 9H), 4.3(d, 1H), 4.56(d, 1H), 5.12(s, 2H), 6.9-7.4(m, 4H), 7.35(s, 5H); B-Isomer, δ=1.1(t, 3H), 1.42(s, 9H), 4.3(d, 1H), 4.54(d, 1H), 5.12(s, 2H), 6.8-7.4(m, 4H), 7.35(s, 5H)

[α]$_D$: A-Isomer, +59.3° (c=1.0%, methanol); B-Isomer, −39.9° (c=0.5%, methanol)

EXAMPLE 3

240 mg of ethyl 3-[2-(1-benzyloxycarbonyl-4-piperidyl)ethoxy]-2(R)-methanesulfonyloxypropionate obtained in Reference Example 10 and 324 mg of tert-butyl 3(R)-amino-4-oxo-2,3,4,5-tetrahydro-1,5-benzothiazepine-5-acetate as prepared by a known method are melted together and heated at 90° C. for 26 hours. After cooling to room temperature, water and ethyl acetate are added to the reaction mixture, and mixture is shaken. The ethyl acetate layer is washed with 3% aqueous phosphoric acid, saline, an aqueous solution of sodium hydrogen carbonate and then with saline, and dried over magnesium sulfate; thereafter, the solvent is distilled off under reduced pressure. The resulting residue is purified by silica gel column chromatography (hexane:ethyl acetate=2:1) to give 160 mg of oily tert-butyl 3(R)-[2-{2-(1-benzyloxycarbonyl-4-piperidyl)ethoxy}-1(S)-ethoxycarbonylethyl]amino-4-oxo-2,3,4,5-tetrahydro-1,5-benzothiazepine-5-acetate.

NMR spectrum (CDCl$_3$; ppm): δ=1.12(t, 3H), 1.49(s, 9H), 4.82(d, 1H), 5.12(s, 2H), 6.96-7.72(m, 4H), 7.34(s, 5H)

[α]$_D$ = −121° (c=1.5%, methanol)

EXAMPLE 4

1.5 g of the A-isomer of ethyl 3-[2-{2-(1-benzyloxycarbonyl-4-piperidyl)ethylthio}-1(R)-ethoxycarbonylethyl]amino-2-oxo-2,3,4,5-tetrahydro-1H-1-benzazepine-1-acetate obtained in Example 1 and 520 μl of anisole are dissolved in 3 ml of acetic acid. To the resulting solution, 7 ml of a solution of 30% hydrogen bromide in acetic acid is added, and this mixture is kept standing at room temperature for 1 hour. To the reaction liquid, 100 ml of isopropyl ether is added, and the mixture is kept standing; thereafter, the supernatant is removed by decantation. The precipitate, after being washed repeatedly with ethyl ether, is dried under reduced pessure to give 1.5 g of dihydrobromide of the A-isomer of ethyl 3-[1(R)-ethoxycarbonyl-2-{2-(4-piperidyl)ethylthio}ethyl]amino-2-oxo-2,3,4,5-tetrahydro-1H-1-benzazepine-1-acetate.

NMR spectrum (DMSO-d$_6$+D$_2$O, ppm): δ=1.2(t and t, 6H), 4.36-4.9(br, 2H), 7.1-7.6(br, 4H)

EXAMPLE 5

1.3 g of the B-isomer of ethyl 3-[2-{2-(1-benzyloxycarbonyl-4-piperidyl)ethylthio}-1(R)-ethoxycarbonylethyl]amino-2-oxo-2,3,4,5-tetrahydro-1H-1-benzazepine-1-acetate obtained in Example 1 and 450 μl of anisole are dissolved in 2.5 ml of acetic acid. To the resulting solution, 6 ml of a solution of 30% hydrogen bromide in acetic acid is added. While treating with a sonication at times at room temperature, the mixture is kept standing for 1 hour. The reaction liquid is treated in the same manner as in Example 4 to give 1.3 g of dihydrobromide of the B-isomer of ethyl 3-[1(R)-ethoxycarbonyl-2-{2-(4-piperidyl)ethylthio}ethyl]amino-2-oxo-2,3,4,5-tetrahydro-1H-1-benzazepine-1-acetate.

NMR spectrum (D$_2$O, ppm): δ=1.19(t, 3H), 1.20(t, 3H), 7.1-7.6(br, 4H)

EXAMPLE 6

1.5 g of dihydrobromide of the A-isomer of ethyl 3-[1(R)-ethoxycarbonyl-2-{2-(4-piperidyl)ethylthio}ethyl]amino-2-oxo-2,3,4,5-tetrahydro-1H-1-benzazepine-1-acetate obtained in Example 4 is dissolved in 10 ml of water. The resulting aqueous solution is added dropwise to 18 ml of an aqueous solution of 2N sodium hydroxide. After stirring for 1 hour at room temperature, 6 ml of methanol is added, and the system further stirred for 1 hour. After neutralizing the reaction liquid with 7.2 ml of acetic acid, the solvent is distilled off under reduced pressure. After concentration, the residue is purified by HP-20 column chromatography (water:methanol=3:1). The effluent is concentrated under reduced pressure, and the resulting residue is recrystalized from 5 ml of water to give 324 mg of the A isomer of 3-[1(R)-carboxy-2-{2-(4-piperidyl)ethylthio}ethyl]amino-2-oxo-2,3,4,5-tetrahydro-1H-1-benzazepine-1-acetic acid monohydrate as a colorless powder.

HPLC (nucleosil$_{10}$C$_{18}$ column; pH 6.4 phosphate buffer:methanol=3:1; flow rate 1.5 ml/min.): retention time=4.6 minutes.

NMR spectrum (DMSO-d$_6$+D$_2$O+DCl, ppm): δ=0.9-2.0(br, 7H), 4.3-4.9(br, 2H), 7.0-7.6(br, 4H)

FD mass spectrum: 450 (M$^+$+1)

[α]$_D$ = +164.0° (c=0.5%, methanol)

Elemental analysis (as C$_{22}$H$_{31}$N$_3$O$_5$S H$_2$O): Calcd: C 56.52; H 7.12; N 8.99 Found: C 57.03; H 7.31; N 9.06

EXAMPLE 7

1.3 g of dihydrobromide of the B-isomer of ethyl 3-[1(R)-ethoxycarbonyl-2-{2-(4-piperidyl)ethylthio}ethyl]amino-2-oxo-2,3,4,5-tetrahydro-1H-1-benzazepine-1-acetate obtained in Example 5 is dissolved in 10 ml of an aqueous solution of 50% methanol, and the resulting solution is gradually added dropwise to 15.5 ml of an aqueous solution of 2N sodium hydroxide. After stirring for 2 hours at room temperature, the reaction liquid is neutralized with 6.5 ml of acetic acid. The residue obtained by concentration under reduced pressure is purified by HP-20 column chromatography (water:methanol=3:1). The solvent is evaporated under reduced pressure, and the resulting residue is lyophilized to give 440 mg of the B-isomer of 3-[1(R)-carboxy-2-{2-(4-piperidyl)ethylthio}ethyl]amino-2-oxo-2,3,4,5-tetrahydro-1H-1-benzazepine-1-acetic acid monohydrate as a colorless powder.

HPLC (nucleosil$_{10}$C$_{18}$ column; pH 6.4 phosphate buffer:methanol=3:1; flow rate 1.5 ml/min.): retention time=6.6 minutes.

NMR spectrum (D$_2$O, ppm): δ=1.0-2.14(br, 7H), 7.0-7.6(br, 4H)

FD mass spectrum: 450 (M$^+$+1)

[α]$_D$ = −92° (c=0.5%, water)

Elemental analysis (as C$_{22}$H$_{31}$N$_3$O$_5$S H$_2$O): Calcd: C 56.52; H 7.12; N 8.99 Found: C 56.45; H 6.90; N 9.04

The melting point of the corresponding anhydride is 235°-240° C. with decomposition when recrystallized from methanol.

EXAMPLE 8

2.3 g of ethyl 3-[2-(1-benzyloxycarbonyl-4-piperidyl)ethoxy]-2(R)-methanesulfonyloxypropionate obtained in Reference Example 10 and 2.9 of tert-butyl 3(S)-amino-2-oxo-2,3,4,5-tetrahydro-1H-1-benzazepine-1-acetate are subjected to the same reaction procedure as in Example 3 to give 2 g of tert-butyl 3(S)-[2-{2-(1-benzyloxycarbonyl-4-piperidyl)ethoxy}-1(S)-ethoxycarbonylethyl]amino-2-oxo-2,3,4,5-tetrahydro-1H-1-benzazepine-1-acetate as an oily substance.

EXAMPLE 9

22 g of the B-isomer of tert-butyl 3-[2-{2-(1-benzyloxycarbonyl-4-piperidyl)ethylthio}-1(R)-ethoxycarbonylethyl]amino-2-oxo-2,3,4,5-tetrahydro-1H-1-benzazepine-1-acetate obtained in Example 2 is subjected to the same reaction procedure as in Example 5 to give 3-[1(R)-ethoxycarbonyl-2-{2-(4-piperidyl)ethylthio}ethyl]amino-2-oxo-2,3,4,5-tetrahydro-1H-1-benzazepine-1-acetic acid dihydrobromide.

EXAMPLE 10

2 g of tert-butyl 3(S)-[2-{2-(1-benzyloxycarbonyl-4-piperidyl)ethoxy}-1(S)-ethoxycarbonylethyl]amino-2-oxo-2,3,4,5-tetrahydro-1H-1-benzazepine-1-acetate is subjected to the same reaction procedure as in Example 5 to give 3(S)-[1(S)-ethoxycarbonyl-2-{2-(4-piperidyl)ethoxy}ethyl]amino-2-oxo-2,3,4,5-tetrahydro-1H-1-benzazepine-1-acetic acid dihydrobromide.

EXAMPLE 11

0.9 g of tert-butyl 3(R)-[2{2-(1-benzyloxycarbonyl-4-piperidyl)ethoxy}-1(S)-ethoxycarbonylethyl]amino-4-oxo-2,3,4,5-tetrahydro-1,5-benzothiazepine-5-acetate obtained in Example 3 is subjected to the same reaction procedure as in Example 5 to give 3(R)-[1(S)-ethoxycarbonyl-2-{2-(4-piperidyl)ethoxy}ethyl]amino-4-oxo-2,3,4,5-tetrahydro-1,5-benzothiazepine-5-acetic acid dihydrobromide.

NMR spectrum (D$_2$O, ppm): $\delta$=1.2(t, 3H), 2.7–3.2(br t, 2H), 7.1–7.9(m, 4H)

EXAMPLE 12

3(S)-[1(S)-ethoxycarbonyl-2-{2-(4-piperidyl)ethoxy}ethyl]amino-2-oxo-2,3,4,5-tetrahydro-1H-1-benzazepine-1-acetic acid dihydrobromide obtained in Example 10 is subjected to the same procedure as in Example 7 to give 1 g of 3(S)-[1(S)-carboxy-2-{2-(4-piperidyl)ethoxy}ethyl]amino-2-oxo-2,3,4,5-tetrahydro-1H-1-benzazepine-1-acetic acid dihydrate as a colorless powder.

HPLC (nucleosil$_{10}$C$_{18}$ column; pH 6.4 phosphate buffer:methanol=3:1; flow rate 1.5 ml/min.): retention time=3.9 minutes.

$[\alpha]_D$ = −158.7° (c=0.5%, water)
FD mass spectrum: 434 (M$^+$ +1)
Elemental analysis (as C$_{22}$H$_{31}$N$_3$O$_6$ 2H$_2$O): Calcd: C 56.28; H 7.51; N, 8.95 Found: C 55.88; H 7.04; N 8.99

EXAMPLE 13

0.8 g of 3(R)-[1(S)-ethoxycarbonyl-2-{2-(4-piperidyl)ethoxy}ethyl]amino-4-oxo-2,3,4,5-tetrahydro-1,5-benzothiazepine-5-acetic acid dihydrobromide obtained in Example 11 is subjected to the same reaction as in Example 7 to give 0.38 g of 3(R)-[1(S)-carboxy-2-{2-(4-piperidyl)ethoxy}ethyl]amino-4-oxo-2,3,4,5-tetrahydro-1,5-benzothiazepine-5-acetic acid.

HPLC (nucleosil$_{10}$C$_{18}$ column; pH 6.4 phosphate buffer:methanol=3:1; flow rate 1.5 ml/min.): retention time=5.2 minutes.

MNR spectrum (D$_2$O, ppm): $\delta$=0.9–2.1(br, 7H), 2.98(br t, 2H), 4.76(d, 1H), 7.1–7.9(m, 4H)

$[\alpha]_D$ = −137.2° (c=0.9%, water)

EXAMPLE 14

6.85 g of S-(1-benzyloxycarbonyl-4-piperidylmethyl)-L-cysteine ethyl ester obtained in Reference Example 12, in place of S-[2-(1-benzyloxycarbonyl-4-piperidyl)ethyl]-L-cysteine ethyl ester, is subjected to the same reaction and treatment procedures as in Example 2 to give 2.3 g of the A-isomer (Rf=0.62; ethyl acetate:hexane=2:1) of tert-butyl 3-[2-(1-benzyloxycarbonyl-4-piperidylmethylthio)-1(R)-ethoxycarbonylethyl]amino-2-oxo-2,3,4,5-tetrahydro-1H-1-benzazepine-1-acetate and 2 g of the B-isomer (Rf=0.53; the same developing solvent as above), each as an oily substance.

NMR spectrum (CDCl$_3$, ppm) of the B-isomer: $\delta$=1.1(t, 3H), 1.43(s, 9H), 4.3(d, 1H), 4.55(d, 1H), 5.12(s, 2H), 6.8–7.4(m, 4H), 7.34(s, 5H)

$[\alpha]_D$ of the B-isomer= −61.1° (c=1%, chloroform)

EXAMPLE 15

1.46 g of ethyl 3-[3-(1-benzyloxycarbonyl-4-piperidyl)propoxy]-2(R)-methanesulfonyloxypropionate obtained in Reference Example 16 and 1.8 g of tert-butyl 3(S)-amino-2-oxo-2,3,4,5-tetrahydro-1H-1-benzazepine-1-acetate prepared by a known method are subjected to the same reaction and treatment procedures as in Example 3 to give 1.6 g of tert-butyl 3(S)-[2-{3-(1-benzyloxycarbonyl-4-piperidyl)propoxy}-1(S)-ethoxycarbonylethyl]amino-2-oxo-2,3,4,5-tetrahydro-1H-1-benzazepine-1-acetate as an oily substance.

NMR spectrum (CDCl$_3$, ppm): $\delta$=1.09(t, 3H), 1.42(s, 9H), 4.58(d, 1H), 6.8–7.4(m, 4H), 7.32(s, 5H)

$[\alpha]_D$ = −77.7° (C=1%, chloroform)

EXAMPLE 16

2 g of the B-isomer of tert-butyl 3-[2-(1-benzyloxycarbonyl-4-piperidylmethylthio)-1R)-ethoxycarbonylethyl]amino-2-oxo-2,3,4,5-tetrahydro-1H-1-benzazepine-1-acetate obtained in Example 14 is subjected to the same reaction and treatment procedures as in Example 5 and then Example 7 to give 0.43 g of the B-isomer of 3-[1(R)-carboxy-2-(4-piperidyl)-methylthioethyl]amino-2-oxo-2,3,4,5-tetrahydro-1H-1-benzazepin-1-acetic acid monohydrate as a colorless powder.

FD mass spectrum: 436 (M$^+$ +1)
$[\alpha]_D$ = −98.1° (c=0.5%, water)
Elemental analysis (as C$_{21}$H$_{29}$N$_3$O$_3$S H$_2$O): Calcd: C 55.62; H 6.89; N 9.27 Found: C 55.25; H 6.77; N 9.11

EXAMPLE 17

1.6 g of tert-butyl 3(S)-[2-{3-(1-benzyloxycarbonyl-4-piperidyl)propoxy}-1(S)-ethoxycarbonylethyl]amino-2-oxo-2,3,4,5-tetrahydro-1H-1-benzazepine-1-acetate obtained in Example 15 is subjected to the same reaction and treatment procedures as in Example 16 to give 0.7 g of 3(S)-[1(S)-carboxy-2-{3-(4-piperidyl)propoxy}ethyl]amino-2-oxo-2,3,4,5-tetrahydro-1H-1-benzazepine-1-acetic acid dihydrate.

FD mass spectrum: 448 (M$^+$ +1)
$[\alpha]_D$ = −108.1° (c=0.5%, methanol)

EXAMPLE 18

1.8 g of ethyl 3-[3-(1-benzyloxycarbonyl-4-piperidyl)propoxy]-2(R)-methanesulfonyloxypropionate obtained in Reference Example 16 is subjected to the same reaction and treatment procedures as in Example 3 to give 1.3 g of tertbutyl 3(R)-[2-{3-(1-benzyloxycarbonyl-4-piperidyl)propoxy}-1(S)-ethoxycarbonylethyl]amino-4- oxo-2,3,4,5-tetrahydro-1,5-benzothiazepin-5-acetate as an oily substance.

NMR spectrum (CDCl$_3$, ppm): δ=1.12(t, 3H), 1.48(s, 9H), 4.81(d, 1H), 5.12(s, 2H), 6.9–7.7(m, 4H), 7.33(s, 5H) [α]$_D$ = −101.6° (c=0.5%, chloroform)

EXAMPLE 19

1.3 g of tert-butyl 3(R)-[2-{3-(1-benzyloxycarbonyl-4-piperidyl)propoxy}-1(S)-ethoxycarbonylethyl]amino-4-oxo-2,3,4,5-tetrahydro-1,5-benzothiazepine-5-acetate obtained in Example 18 is subjected to the same reaction and treatment procedure as in Example 16 to give 0.6 g of 3(R)-[1(S)-carboxy-2-{3-(4-piperidyl)propoxy}ethyl]amino-4-oxo-2,3,4,5-tetrahydro-1,5-benzothiazepine-5-acetic acid.

HPLC (nucleosil$_{10}$C$_{18}$ column; pH 6.4 phosphate buffer:methanol=3:1; flow rate 1.5 ml/min.): retention time 6.1 minutes.

FD mass spectrum: 466 (M+ +1) [α]$_D$ = −132.9° (c=1%, water)

EXAMPLE 20

3(S)-[1(S)-Carboxy-2-(4-piperidyl)oxyethyl]amino-2-oxo-2,3,4,5-tetrahydro-1H-1-benzazepine-1-acetic acid

EXAMPLE 21

3(R)-[1(S)-Carboxy-2-(4-piperidyl)methoxyethyl]amino-4-oxo-2,3,4,5-tetrahydro-1,5-benzothiazepine-5-acetic acid

EXAMPLE 22

3(R)-[1(S)-Carboxy-2-(4-piperidyl)oxyethyl]-amino-4-oxo-2,3,4,5-tetrahydro-1,5-benzothiazepine-5-acetic acid

EXAMPLE 23

3(R)-[1(S)-Carboxy-3-{2-(4-piperidyl)ethoxy}propyl]amino-4-oxo-2,3,4,5-tetrahydro-1,5-benzothiazepine-5-acetic acid

EXAMPLE 24

3(S)-[1(S)-Carboxy-2-(4-piperidyl)methoxyethyl]amino-2-oxo-2,3,4,5-tetrahydro-1H-1-benzazepine-1-acetic acid

EXAMPLE 25

3-[1(R)-Carboxy-2-(4-piperidyl)thioethyl]amino-2-oxo-2,3,4,5-tetrahydro-1H-1-benzazepine-1-acetic acid

EXAMPLE 26

3-[1(R)-Carboxy-2-{3-(4-piperidyl)propylthio}ethyl]amino-2-oxo-2,3,4,5-tetrahydro-1H-1-benzazepine-1-acetic acid

EXAMPLE 27

3(S)-[1(S)-Carboxy-3-{2-(4-piperidyl)ethoxy}propyl]amino-2-oxo-2,3,4,5-tetrahydro-1H-1-benzazepine-1-acetic acid

EXAMPLE 28

3[1(S)-Carboxy-3-{2-(4-piperidyl)ethylthio}propyl]amino-2-oxo-2,3,4,5-tetrahydro-1H-1-benzazepine-1-acetic acid

EXAMPLE 29

3(S)-[1(R)-Carboxy-2-{2-(4-piperidyl)ethylthio]ethyl]amino-4-oxo-2,3,4,5-tetrahydro-1,5-benzoxazepine-5-acetic acid

EXAMPLE 30

3(S)-[1(S)-Carboxy-2-{2-(4-piperidyl)ethoxy}ethyl]amino-4-oxo-2,3,4,5-tetrahydro-1,5-benzoxazepine-5-acetic acid The present invention has been fully explained in the description and examples given above, but any variations and modifications thereof may be made without departing from the spirit and scope of the present invention.

We claim:

1. A piperidine compound of the formula:

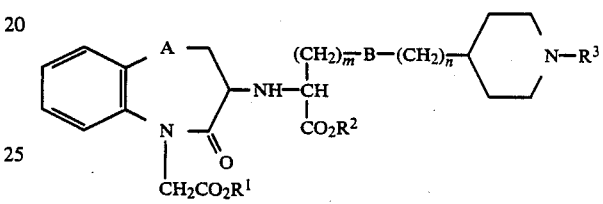

wherein A represents a methylene group, an oxygen atom or a sulfur atom; B represents an oxygen atom or a sulfur atom; R$^1$ and R$^2$ independently represent a hydrogen atom, a lower alkyl group or an aralkyl group; R$^3$ represents a hydrogen atom or an amino protective group; m represents 1 or 2; and n represents an integer of 0 to 3, or a pharmaceutically acceptable salt thereof.

2. A piperidine compound as claimed in claim 1, wherein said compound is selected from the group consisting of 3-[1(R)-carboxy-2-{2-(4-piperidyl)ethylthio}ethyl]amino-2-oxo-2,3,4,5-tetrahydro-1H-1-benzazepine-1-acetic acid, 3-[1(R)-ethoxycarbonyl-2-{2-(4-piperidyl)ethylthio}ethyl]amino-2-oxo-2,3,4,5-tetrahydro-1H-1-benzazepine-1-acetic acid, 3(S)-[1(S)-ethoxycarbonyl-2-{2-(4-piperidyl)ethoxy}ethyl]amino-2-oxo-2,3,4,5-tetrahydro-1H-1-benzazepine-1-acetic acid, 3(R)-[1(S)-ethoxycarbonyl-2-{2-(4-piperidyl)ethoxy}amino-4-oxo-2,3,4,5-tetrahydro-1,5-benzothiazepine-5-acetic acid, 3(S)-[1(S)-carboxy-2-{2-(4-piperidyl)ethoxy}ethyl]amino-2-oxo-2,3,4,5-tetrahydro-1H-1-benzazepine-1-acetic acid, 3(R)-[1(S)-carboxy-2-{2-(4-piperidyl)ethoxy}ethyl]amino-4-oxo-2,3,4,5-tetrahydro-1,5-benzothiazepine-5-acetic acid, 3-{1(R)-carboxy-2-(4-piperidyl)methylthioethyl}amino-2-oxo-2,3,4,5-tetrahydro-1H-1-benzazepine-1-acetic acid, 3(S)-[1(S)-carboxy-2-{3-(4-piperidyl)propoxy}ethyl]amino-2-oxo-2,3,4,5-tetrahydro-1H-1-benzazepine-1-acetic acid, 3(R)-[1(S)-carboxy-2-{3-(4-piperidyl)propoxy}ethyl]amino-4-oxo-2,3,4,5-tetrahydro-1,5-benzothiazepine-5-acetic acid, and a pharmaceutically acceptable salt thereof.

3. A pharmaceutical composition which comprises a therapeutically effective amount of the piperidine compound as claimed in claim 1 or 2 with a pharmaceutically acceptable additive.

* * * * *